(12) United States Patent
Lee et al.

(10) Patent No.: US 6,924,111 B2
(45) Date of Patent: Aug. 2, 2005

(54) MICROARRAY SUBSTRATE COMPRISING PATTERNED PHOTORESIST FILM WITH SPOT REGIONS, MICROARRAY, AND METHOD OF DETECTING TARGET MATERIAL

(75) Inventors: Soo-suk Lee, Gyeonggi-do (KR); Sun-hee Kim, Gyeonggi-do (KR); Young Choi, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 10/761,516

(22) Filed: Jan. 20, 2004

(65) Prior Publication Data

US 2004/0146920 A1 Jul. 29, 2004

(30) Foreign Application Priority Data

Jan. 20, 2003 (KR) .................... 10-2003-0003669

(51) Int. Cl.[7] ................................................ C12Q 1/68
(52) U.S. Cl. .................... 435/6; 435/7.1; 435/962; 436/518; 436/525; 436/535
(58) Field of Search .................... 436/518, 524–536; 427/287, 387, 407; 435/6–7.92

(56) References Cited

U.S. PATENT DOCUMENTS

| | | | |
|---|---|---|---|
| 5,445,934 A | 8/1995 | Fodor et al. ............... 435/6 |
| 5,744,305 A | 4/1998 | Fodor et al. ............... 435/6 |
| 6,159,681 A | * 12/2000 | Zebala ............... 435/4 |
| 6,365,418 B1 | * 4/2002 | Wagner et al. ............... 436/518 |
| 6,376,619 B1 | * 4/2002 | Halverson et al. ....... 525/330.3 |
| 6,406,844 B1 | * 6/2002 | Pirrung et al. ............... 435/6 |
| 6,406,921 B1 | * 6/2002 | Wagner et al. ............... 436/518 |
| 6,416,952 B1 | * 7/2002 | Pirrung et al. ............... 435/6 |

OTHER PUBLICATIONS

Argitis et al, Patterning of biomolecules with a new photolithographic methodology, Dec. 2002, China—EU Forum on Nanosized Technology, p. 245–250.*

Douvas et al, Biocompatible photolithographic process for the patterning of biomolecules, 2002, Biosensors & Bioelectronics, 17, 269–278.*

Bao et al, Toward controllable self–assembly of microstructures: selective functionalization and fabrication of patterned spheres, Dec. 2001, Chem Matters, 14, 24–26.*

Chrisey et al, Fabrication of patterned DNA surfaces, 1996, Nucleic Acids Research, 24(15), p. 3040–3047.*

* cited by examiner

Primary Examiner—Long V. Le
Assistant Examiner—Nelson Yang
(74) Attorney, Agent, or Firm—Cantor Colburn LLP

(57) ABSTRACT

Provided is a microarray substrate. The microarray substrate includes a patterned photoresist film having one or more spot regions therein. The photoresist film can be detached from the substrate.

2 Claims, 3 Drawing Sheets

A  B

MICROARRAY SUBSTRATE COMPRISING PATTERNED PHOTORESIST FILM WITH SPOT REGIONS, MICROARRAY, AND METHOD OF DETECTING TARGET MATERIAL

BACKGROUND OF THE INVENTION

This application claims the priority of Korean Patent Application No. 2003-3669, filed on Jan. 20, 2003, in the Korean Intellectual Property Office, the disclosure of which is incorporated herein in its entirety by reference.

1. Field of the Invention

The present invention relates to a microarray substrate having a patterned photoresist film with spot regions, a microarray, and a method of detecting a target material using the microarray.

2. Description of the Related Art

Generally, the term, "microarray" indicates an analysis system in which polymer molecules such as polynucleotides and proteins are immobilized in a high density on a solid substrate. The polymer molecules are immobilized on the spot regions which is arranged in an array. Such a microarray has been well known in the pertinent art. Examples of the microarray are disclosed in U.S. Pat. Nos. 5,445,934 and 5,744,305. Examples of the microarray include a protein array and a polynucleotide array. The term, "spot regions of the microarray" indicates regions on the microarray where polymer molecules such as proteins and polynucleotides are immobilized.

Generally, biological molecules, also called "probe molecules", specifically bound to target materials, are mainly used as the polymer molecules immobilized on the microarray. The microarray has been usefully applied in a method of detecting target molecules and the like. According to an example of the method of detecting target molecules using a microarray, samples containing target nucleotides are spotted on the microarray having immobilized oligonucleotide probes thereon, followed by hybridization under a hybridization condition. After the hybridization is completed, the degree of hybridization is assessed by monitoring the intensity of a signal, such as light. Generally, the target molecules are labeled with detectable materials.

However, such a conventional microarray method for detecting target materials is accompanied by problems associated with nonspecific binding. As used herein, the term, "nonspecific binding" indicates the binding of target materials to other compounds on a microarray, for example, surface molecules of a substrate, in addition to probe molecules. Such nonspecific binding of target materials reduces the sensitivity of a signal to be measured, thereby causing a detection error.

As a conventional way to prevent the nonspecific binding of target materials, a method of coating a blocking material on a microarray during fabrication of the microarray or signal detection is used. For example, bovine serum albumin (BSA) is used as the blocking material. BSA serves to quench unreacted activated coupling compounds to minimize nonspecific binding. For this, BSA is coated in a monolayer on a solid substrate. However, the use of BSA may face with unexpected nonspecific binding problem according to the coating condition of BSA, for example, the concentration and duration of the coating. Also, immobilized molecules, i.e., probes may be distorted, which is known as "tailing". In addition, there arises a problem in that compounds such as BSA are easily damaged by heat or chemicals.

FIG. 1 is a schematic diagram that illustrates a conventional microarray preparation method using BSA as a material for preventing the nonspecific binding of a target material. First, a coupling compound 10 is coated on a glass substrate 2. An example of the coupling compound is a silane compound with an end group such as aldehyde, epoxy, and amine. A primary antibody as a probe 12 is covalently bound to the coupling compound. Then, in order to prevent the nonspecific binding of the target material, BSA 14 is coated on the coupling compound as a blocking material for blocking the activation of the coupling compound unreacted with the probe 12. The microarray thus prepared can be used to directly detect an antigen which is the target material or to detect a secondary antibody using the antigen bound to the primary antibody.

As another method for preventing the nonspecific binding of a target material, in fabrication of a DNA chip, there is mainly used a method of coating an anionic chemical material on a solid substrate having an immobilized DNA probe thereon. However, this method also faces with a problem of lack of uniformity in terms that the degree of preventing the nonspecific binding varies depending on a coating condition. Also, the anionic chemical material is little used in a protein microarray because the activity of immobilized protein can be inhibited.

In addition, there is a method of using a probe containing polyethyleneglycol (PEG) or a polymer like PEG. However, this method has problems in that fabrication of the PEG-containing probe or a microarray containing the probe is complicated, a fabrication unit cost is high, and complete prevention of nonspecific binding is difficult.

SUMMARY OF THE INVENTION

The present invention provides a microarray substrate capable of efficiently preventing the nonspecific binding of a target material even when a compound such as a blocking material is not used.

The present invention also provides a microarray based on the microarray substrate capable of reducing the nonspecific binding of a target material.

The present invention also provides a method of detecting a target material capable of efficiently preventing the nonspecific binding of the target material even when a compound such as a blocking material is not used.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
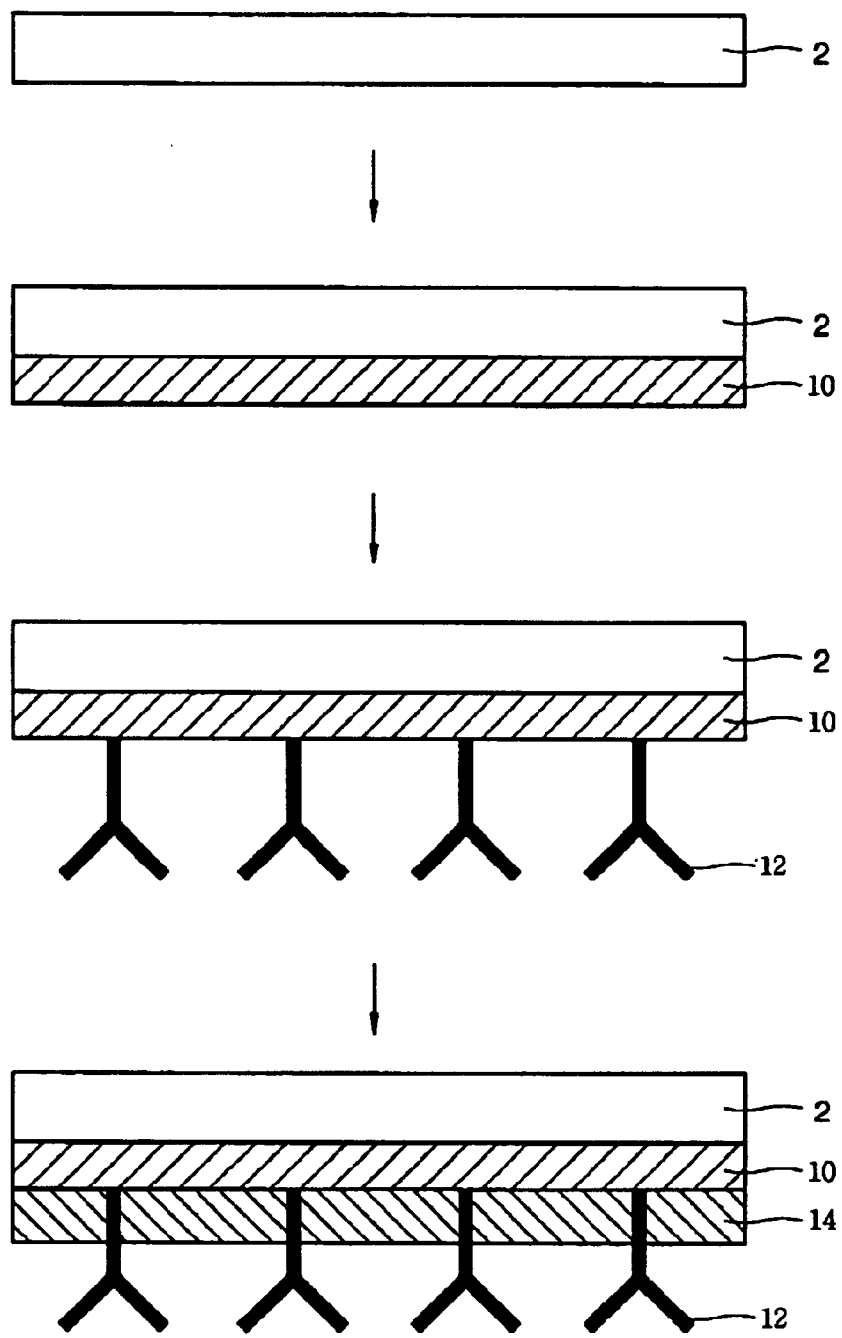
FIG. 1 is a schematic diagram that illustrates a analysis method with conventional microarray using bovine serum albumin (BSA) as a material for preventing the nonspecific binding of a target material.

The present invention provides a micorarray substrate including a patterned photoresist film having one or more spot regions therein. The photoresist film is detachable from the substrate.

The microarray substrate may further include, in the spot regions, a plurality of compounds having functional groups capable of covalently binding to probes. The microarray substrate may be made of a material such as glass, silicon, polypropylene, and polyethylene. The probes are specifically bound to a target material to be detected, and may be, but are not limited to, proteins, nucleotides, or polysaccharides. Also, any functional groups may be used provided that they can be attached with the probes. For example, the functional groups may be aldehyde, epoxy, or amine groups. The compounds having these functional groups may be silane compounds with end groups such as aldehyde, epoxy, and amine. Examples of silane comounds with amino end groups include, but are not limited to, 3-aminopropyltrimethoxysilane, γ-aminopropyltriethoxy silane (GAPS), and γ-aminopropyldiiethoxy silane (GAPDES).

The present invention also provides a microarray including the probes immobilized at the spot regions of the microarray substrate. These probes can be immobilized by covalent bond, ionic bond, or physical adsorption. The immobilization of the probes on the microarray substrate has been well known in the pertinent art. For example, probe molecules such as proteins or nucleotides activated by compounds such as carbodiimides may be immobilized by coupling them with an aminated substrate.

According to the present invention, the photoresist film is of thin film type and can be detached from the substrate without being damaged. As used herein, the term, "detach" or similar expressions, indicates the physical separation of the photoresist film from the microarray substrate. In this regard, the photoresist film of the present invention can be detached from the substrate after the hybridization between the probes and the target materials at the spot regions to reduce nonspecific reaction. As used herein, the term, "photoresist" indicates a photosensitive material commonly used in a semiconductor fabrication process. In detail, the photoresist indicates a material exhibiting a change in physical properties, such as solubility change in a specific solvent, i.e., solubilization or insolubilization, due to an instant change of its molecular structure induced by irradiation. The photoresist as used herein allows for easy processing of the spot regions using photolithography in fabrication of the microarray substrate. At the same time, the photoresist serves as a blocking material that prevents the nonspecific binding of the target material.

The photoresist as used herein may be that commonly used in a semiconductor fabrication process. For example, the photoresist may be diazonaphtoquinone-novolac resin (DNA/NR) or BF410 (Tokyo Oka, Japan).

The photoresist film may be formed by a coating method well known to ordinary persons skilled in the art. For example, spin coating, dip coating, or immersion coating may be used.

The spot regions may be formed by a method commonly used in a semiconductor fabrication process, for example, photolithography. For example, a positive photoresist is coated on a substrate, followed by irradiation and developing, to remove a photoresist intended for the spot regions on the substrate.

Figure 2:
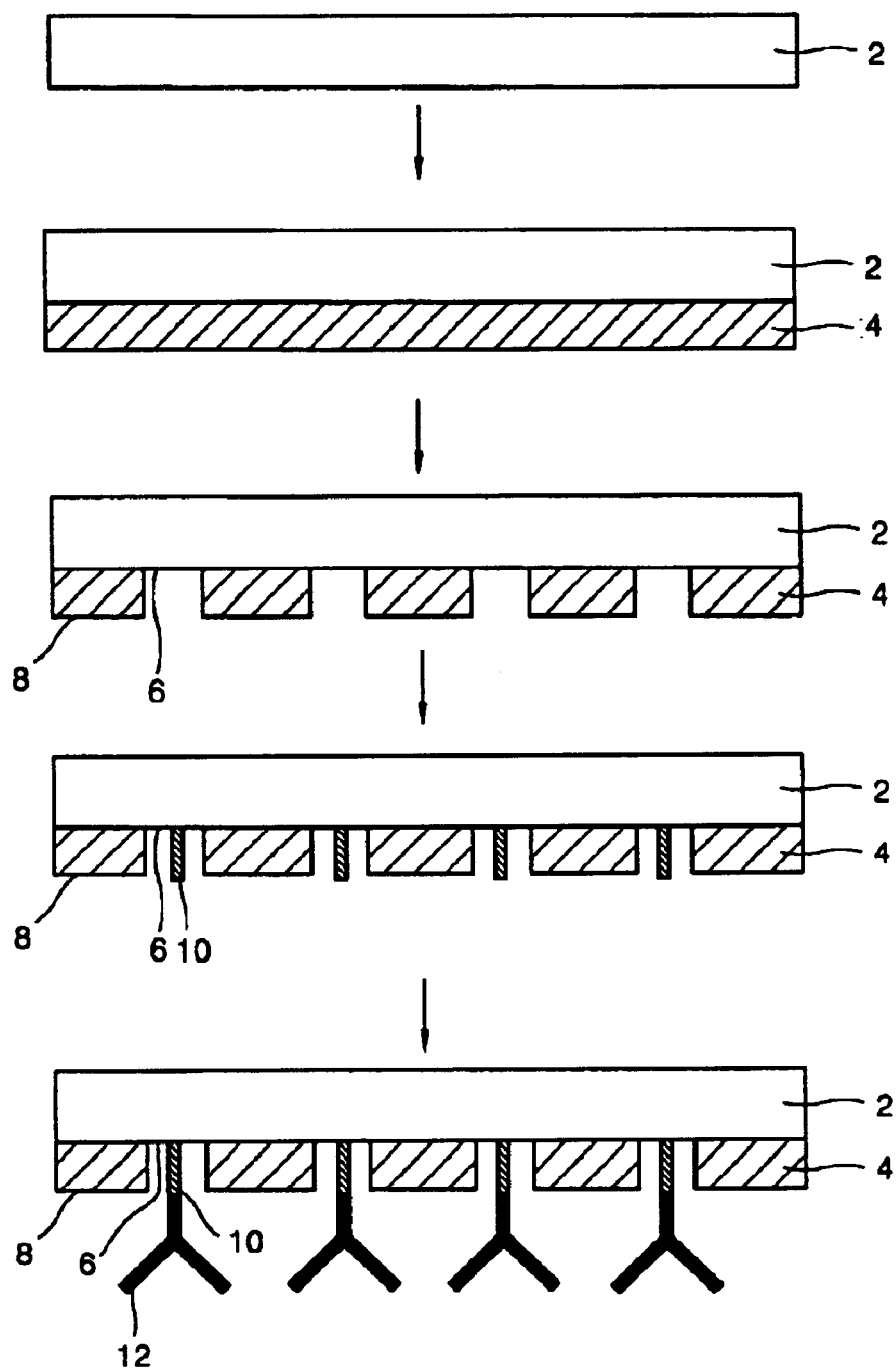
FIG. 2 is a schematic diagram that illustrates a microarray preparation method using a patterned photoresist film with spot regions according to the present invention.

An example of a method of patterning a photoresist film for spot regions on a substrate will now be described with reference to FIG. 2.

First, a photoresist is coated on a glass substrate 2 to form a photoresist film 4. The photoresist film thus formed is patterned by photolithography to form spot regions 6. Regions between the spot regions 6 are called border regions 8. Accordingly, a microarray having the spot regions 6 and the border regions 8 can be prepared. In this state, a coupling agent 10 to be bound to probes can be located at the spot regions. For example, the coupling agent 10 may be a silane compound with an aldehyde end group. Then, the probes 12 are bound to the coupling agent 10. Accordingly, the microarray having the probes immobilized on the substrate is completed.

The present invention also provides a method of detecting a target material, including:

(a) preparing a substrate having a patterned photoresist film, the patterned photoresist film being detachable from the substrate and having one or more spot regions therein;

(b) immobilizing probes in the spot regions to prepare a microarray;

(c) contacting the probes and a sample containing the target material to react the probes and the target material;

(d) detaching the photoresist film from the microarray to remove the target material nonspecifically bound to the photoresist film; and (e) detecting the reaction between the target material and the probes.

According to the method of the present invention, the probes are specifically bound to the target material, and may be proteins, nucleotides, or polysaccharides. In detail, the probes may be DNAs, RNAs, antibodies, antigens, ligands, substrates, or inhibitors. As described above, the immobilization of the probes on the substrate can be carried out by a method well known to ordinary persons skilled in the art. For example, the probes may be immobilized on the substrate by activating the surface of the substrate using a silane compound with an end group such as aldehyde, epoxy, and amine, and then covalently bonding a probe material activated with a compound such as carbodiimide to the activated surface of the substrate. In addition to such a covalent bond, the probe material may be immobilized by ionic bond or physical adsorption.

According to the method of the present invention, the sample containing the target material contacts with the probes. Generally, the sample of a liquid phase contacts with the probes in a condition appropriate to induce the reaction between the target material and the probes. For example, in the case of detecting a nucleotide target material, nucleotide probes and target nucleotides are incubated in a condition of optimal temperature and salt concentration that can induce the hybridization between the nucleotide probes and the target nucleotides. When specific reaction between the target material and the probes is completed, unreacted reactants are removed by washing.

According to the method of the present invention, the photoresist film is of thin film type and can be physically separated from the substrate without being damaged. The reaction between the target material and the probes occurs in the spot regions. The photoresist film is made up of the border regions between the spot regions. Therefore, the separation of the photoresist film enables to removal of the target material nonspecifically bound to the border regions between the spot regions.

Step (e) of detecting the reaction between the target material and the probes may be carried out by various methods. A method of detecting an optical, electrical, or color signal may be used. An optical detection method is preferred. According to an optical detection method, the target material is generally labeled with an optically detectable element. The reaction results between the target material and the probes can be detected by measuring light emitted from a reaction product of the target material and the probes by irradiation of excitation light.

EXAMPLE

First, a photoresist BF410 (Tokyo Oka, Japan) of a film type was coated on a glass substrate to form a photoresist film. The photoresist film thus formed was patterned by photolithography to form spot regions. A microarray thus prepared was incubated in a UV-Ozone cleaner for one hour and then activated so that the spot regions have —SiOH groups. The activated spot regions were filled with a 3% toluene solution of 3-(glycidoxypropyl)trimethoxysilane and then incubated at room temperature for one hour.

When the silanation process was completed, the microarray was washed with toluene and dried in an about 120° C. oven for one hour. Then, the microarray was cooled to room temperature, washed with toluene once again, and dried at room temperature.

Next, the spot regions of the microarray were filled with a Human IgG phosphate buffered saline (PBS) solution (100 mg/ml, each 10 mL) and then incubated at room temperature for one hour. After the microarray was washed with a 1% Tween 20 PBS solution, an Anti-human IgG-FITC conjugate PBS solution (100 mg/ml) was dropwise added to each of the spot regions and then incubated at room temperature for 30 minutes. Then, the microarray was washed with a 1% Tween 20 PBS solution and then distilled water.

Figure 3:
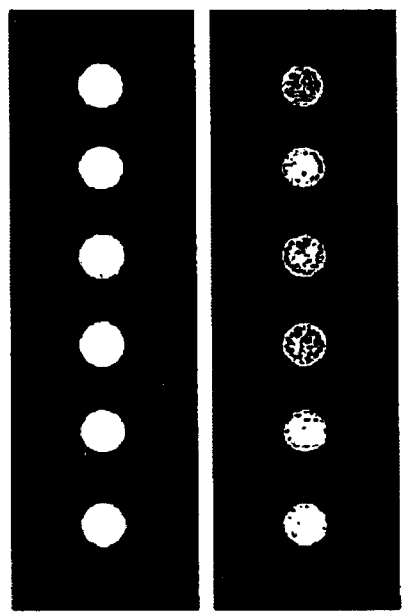
FIG. 3 is a photograph showing the target material detection results using a microarray having a patterned photoresist film with spot regions according to the present invention.
Figure 3:
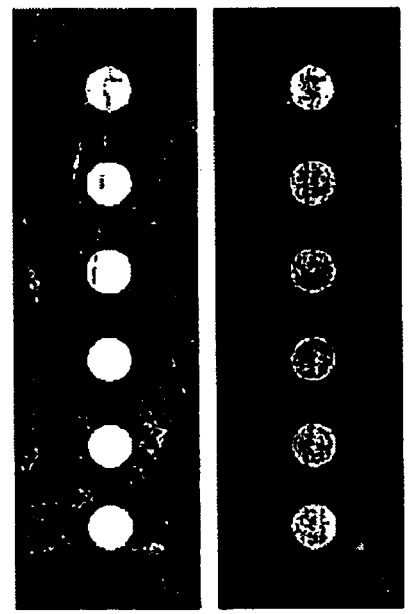

After the reaction was completed, the photoresist film was carefully delaminated from the microarray. A reaction result was assessed by a scanner and is shown in FIG. 3A. FIG. 3B shows the reaction result of a control using BSA as a material for preventing nonspecific binding. In each of FIGS. 3A and 3B, a left reaction result is a result scanned at a high resolution relative to a right reaction result. As seen from FIGS. 3A and 3B, the microarray of the present invention exhibited excellent inhibition effect of nonspecific binding, as compared to the microarray using BSA.

As apparent from the above descriptions, the microarray substrate of the present invention can be effectively applied in preparing a microarray capable of preventing nonspecific binding even when a blocking material such as BSA is not used.

The microarray of the present invention can be efficiently applied in a microarray assay requiring significant reduction of the nonspecific binding of a target material.

The present invention also provides a method of efficiently detecting a target material without using BSA as a material for preventing nonspecific reaction.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting a target material, comprising:
   (a) preparing a substrate having a patterned photoresist film, the patterned photoresist film being detachable from the substrate and having one or more spot regions therein, wherein the spot regions are defined by the patterned photoresist film;
   (b) immobilizing probes in the spot regions to prepare a microarray;
   (c) contacting the probes and a sample containing the target material to react the probes and the target material;
   (d) detaching the photoresist film from the microarray to remove the target material nonspecifically bound to the photoresist film, wherein detecting comprises delamating; and
   (e) detecting the reaction between the target material and the probes.

2. The method of claim 1, wherein the probes are proteins, nucleotides, or polysaccharides.

* * * * *